(12) United States Patent
Court et al.

(10) Patent No.: US 6,981,506 B2
(45) Date of Patent: *****Jan. 3, 2006

(54) BANDAGING SYSTEM

(75) Inventors: Andrew D. Court, South Wirral (GB); Douglas Queen, Buckinghamshire (GB)

(73) Assignee: Bristol-Myers Squibb Company, New York, NY (US)

( * ) Notice: Subject to any disclaimer, the term of this patent is extended or adjusted under 35 U.S.C. 154(b) by 23 days.

This patent is subject to a terminal disclaimer.

(21) Appl. No.: 10/818,319

(22) Filed: Apr. 5, 2004

(65) Prior Publication Data

US 2004/0199096 A1    Oct. 7, 2004

Related U.S. Application Data

(62) Division of application No. 09/068,634, filed as application No. PCT/EP96/05017 on Nov. 15, 1996, now Pat. No. 6,759,566.

(51) Int. Cl.
*A61F 13/00*    (2006.01)

(52) U.S. Cl. ......................... 128/888; 128/898; 602/42; 602/75; 602/79

(58) Field of Classification Search ............ 602/41–42, 602/53, 75, 79; 128/888, 898
See application file for complete search history.

(56) References Cited

U.S. PATENT DOCUMENTS

| | | | |
|---|---|---|---|
| 2,649,088 A | * | 8/1953 | Sigg |
| 4,542,739 A | | 9/1985 | Schafer et al. |
| 4,957,795 A | * | 9/1990 | Riedel .......................... 428/74 |
| 4,984,570 A | | 1/1991 | Langen et al. |
| 5,005,567 A | * | 4/1991 | Gilman et al. |

FOREIGN PATENT DOCUMENTS

| | | |
|---|---|---|
| WO | WO 9402090 A | 2/1994 |
| WO | WO 9412133 A | 6/1994 |
| WO | WO 94 16746 A | 8/1994 |
| WO | WO 9417227 A | 8/1994 |

* cited by examiner

*Primary Examiner*—Michele Kidwell
(74) *Attorney, Agent, or Firm*—John M. Kilcoyne

(57) ABSTRACT

A bandaging system for use in the treatment of a patient with a venous leg ulcer comprising as an inner layer in the system a highly absorbent bandage which bandage comprises at least 5% by weight of a highly absorbent fiber and as a further layer in the system an elastic bandage.

12 Claims, No Drawings

BANDAGING SYSTEM

This is a divisional application of application Ser. No. 09/068,634, filed July 13, 1998, which is now U.S. Pat. No. 6,759,566 which is a 371 of PCT/EP96/05017 filed Nov. 15, 1996.

This invention concerns a bandaging system and in particular a bandaging system for use in the treatment of venous leg ulcers.

In the past it has been common to treat venous leg ulcers with a four layer system of bandaging, these layers comprising:

(i) an inner layer of absorbent orthopaedic wool for exudate absorption and pressure redistribution;

(ii) a second layer of crepe bandage to apply low pressure to the limb;

(iii) a third layer of elastic bandage to apply additional pressure to the limb; and (iv) a cohesive self-adherent bandage to secure the system in place. Such a bandaging system is described in "The Function of Multiple Layer Compression Bandaging in the Management of Venous Ulcers", DDI Wright et al, SWM, 10, 109–10 1988.

While compression bandaging of the type described above can accelerate healing of leg ulcers, the system has several disadvantages. These are that the application of four layers of bandaging is costly, time consuming, needs to be performed by trained and experienced staff and must be repeated at least weekly.

We have now found that it is possible to reduce the number of layers of bandaging needed in a system by use of a highly absorbent bandage in combination with an elastic bandage.

Accordingly the present invention provides a bandaging system for use in the treatment of a patient with a venous leg ulcer the system comprising as an inner layer in the system a highly absorbent bandage which bandage comprises at least 5% by weight of a highly absorbent fibre and as a further layer in the system an elastic bandage.

The use of a highly absorbent bandage in the bandaging system gives the advantage that the number of layers can be reduced whilst maintaining even pressure distribution and a seven day wear time by the patient.

The bandaging system is preferably a compression bandaging system which comprises an elastic bandage of the type disclosed in PCT/GB 93/02469 to Brightwake Ltd or that marketed under the name SETOPRESS™ by Seton Healthcare Group of Oldham, England or that marketed under the name TENSOPRESS™ by Smith and Nephew Ltd. We have found in a preferred embodiment of the invention that the bandaging system can consist of two layers, one being the highly absorbent bandage and the other being an elastic compression bandage capable of generating a pressure of 25–40 mmHg at the ankle and 15–20 mmHg at the calf.

The advantage of using a highly absorbent bandage in this manner is that the bandage is capable of absorbing and retaining exudate under the conditions of sub-bandage pressure encountered in compression bandaging. This ability to handle and retain exudate at sub-bandage pressure is not generally exhibited by bandages commonly used for ulcer treatment.

In the context of the present invention by highly absorbent is meant that the fibre or bandage will absorb and retain exudate under typical sub-bandage pressures, at least 25 g/g of water.

Suitable highly absorbent fibres for use in the bandage of the system of the present invention include OASIS™ fibre as disclosed in EP 0269393 A, modified cellulose fibres as described in WO93/12275 to Courtaulds Plc or GB9301258 to Courtaulds Plc and alginate fibres as described in WO 94/17227 to E. R. Squibb and Sons.

Preferably the highly absorbent bandage comprises at least 5% of highly absorbent fibre the balance of the bandage comprising cotton or viscose of ordinary absorbency. More preferably the bandage comprises between 50% and 50% of highly absorbent fibre, more preferably 10% to 15%.

Preferably the highly absorbent bandage comprises up to 10% of a bicomponent fibre for example DANAKLON ES-C-PHIL™ a polyolefin bicomponent fibre ex Danaklon of Varde, Denmark.

The invention will now be illustrated by the following Examples.

EXAMPLE 1

A highly absorbent bandage as used in the bandaging system according to the invention was made by preblending three component fibres Oasis™, DANAKLON ES-C-PHIL™ and viscose in the required percentages and then carding to form a batt. The batt was cross-laid to the desired thickness before passing through a needle loom where the batt was needled to impart structural integrity. The resultant web was heat treated in a tunnel oven to thermally bond the fabric. The resultant stock was slit and cut to the required size for bandages.

EXAMPLE 2

The effect of pressure on the fluid uptake and fluid retention capabilities of a highly absorbent bandage as used in the bandaging system of the invention were compared to those of commercially available orthopaedic wadding (an example of which is Velband which is commonly used as layer one in a four layer bandaging system) in the following way.

The fluid uptake of samples of wadding size 5 cm×5 cm was measured by immersing the wadding in water for 30 minutes at 37° C. The fluid uptake of the samples was calculated in terms of weight uptake per sample weight (g/g) and weight uptake per unit area (g/cm$^2$).

The fluid retention of the samples was measured by placing 100 cm$^2$ samples on a stainless steel tray and immersing them in water at 20° C. for 10 seconds and allowing them to drain for 30 seconds. A 2 kg weight was applied over the total area for 30 seconds and the fluid uptake of the samples calculated in units of weight uptake per sample weight (g/g) and weight uptake per unit area (g/cm$^2$). The results are presented in the following tables in which:

Bandage 101 is a bandage comprising a mix of 90% viscose and 10% Danaklon as made by the method described in Example 1 except that the highly absorbent fibre was omitted.

Bandage 102 is a bandage as used in the system according to the invention comprising a mix of 78% viscose, 12% Oasis and 10% Danaklon as made by the method described in Example 1.

Cellona™, Lantor Synthetics™, Soffban™, Softexe™, Velband™ and Webril™ are commercially available orthopaedic wadding materials from various manufacturers. Velband™ is commonly used as the inner layer in the four layer bandaging system of the prior art referred to above.

CoV is the Coefficient of Variation and is a measure of the degree of variation in the results for a particular bandage.

|  | Fluid Uptake (g) | | | Fluid Uptake (g/cm2) | | | Fluid Uptake (g/g) | | |
|---|---|---|---|---|---|---|---|---|---|
| Bandage | Mean | SD | CoV | Mean | SD | CoV | Mean | SD | CoV |
| Pressure = 0 mmHg, Test Fluid = Water | | | | | | | | | |
| Bandage 101 | 3.755 | 0.200 | 5.334 | 0.150 | 0.008 | 5.334 | 18.093 | 1.242 | 6.865 |
| Bandage 102 | 5.941 | 0.566 | 9.524 | 0.238 | 0.023 | 9.524 | 29.605 | 1.114 | 3.763 |
| Cellona | 5.409 | 0.244 | 4.519 | 0.216 | 0.010 | 4.519 | 24.313 | 0.779 | 3.203 |
| Lantor Synthetic | 5.571 | 0.517 | 9.280 | 0.223 | 0.021 | 9.280 | 23.090 | 1.227 | 5.315 |
| Soffban | 4.504 | 0.403 | 8.949 | 0.180 | 0.016 | 8.949 | 22.809 | 2.001 | 8.772 |
| Softexe | 5.886 | 0.752 | 12.782 | 0.235 | 0.030 | 12.782 | 29.138 | 2.519 | 8.647 |
| Velband | 4.482 | 0.293 | 6.532 | 0.179 | 0.012 | 6.532 | 15.710 | 0.975 | 6.206 |
| Webril | 3.490 | 0.135 | 3.863 | 0.140 | 0.005 | 3.863 | 15.215 | 0.468 | 3.076 |
| Pressure = 15 mmHg, Test Fluid = Water | | | | | | | | | |
| Bandage 101 | 13.384 | 2.074 | 15.492 | 0.134 | 0.021 | 15.492 | 15.560 | 1.125 | 7.231 |
| Bandage 102 | 27.090 | 0.861 | 3.179 | 0.278 | 0.009 | 3.179 | 30.422 | 1.301 | 4.275 |
| Cellona | 18.638 | 1.049 | 5.630 | 0.186 | 0.010 | 5.630 | 20.891 | 1.552 | 7.427 |
| Lantor Synthetic | 20.448 | 0.460 | 2.289 | 0.201 | 0.005 | 2.289 | 22.762 | 0.796 | 3.495 |
| Soffban | 15.130 | 1.649 | 10.901 | 0.151 | 0.016 | 10.901 | 17.997 | 1.092 | 6.070 |
| Softexe | 19.258 | 0.790 | 4.101 | 0.193 | 0.008 | 4.101 | 21.786 | 1.022 | 4.692 |
| Velband | 18.067 | 0.318 | 1.757 | 0.181 | 0.003 | 1.757 | 14.610 | 0.134 | 0.917 |
| Webril | 14.602 | 0.218 | 1.733 | 0.126 | 0.002 | 1.733 | 13.009 | 0.329 | 2.526 |

These results show that a highly absorbent bandage suitable for use in a bandaging system according to the invention has a greater fluid absorbtion and retention capability under pressure than conventional orthopaedic wadding. The improved fluid handling properties of the highly absorbent bandage when used in a bandaging system according to the invention enables the number of layers to be reduced while maintaining a 7 day wear time for the user.

From the results this is clearly seen in the fluid uptake figures presented as g/g. These figures are a more reliable guide than either the fluid uptake g or fluid uptake g/cm2 figures as these do not allow for variations in sample thickness. For example the highly absorbent bandage for use in the system according to the invention (Bandage 102) has a fluid uptake at 0 mmHg of 29.605 g/g. At 15 mmHg this increases to 30.422 g/g. The closest conventional bandage in terms of results is Softexe™ which has a fluid uptake at 0 mmHg of 29.138 g/g. At 15 mmHg this decreases to 21.786 g/g. All of the other orthopaedic waddings, including Velband™, show a decrease in fluid retention under pressure.

EXAMPLE 3

In use the bandaging system is applied to the leg of a patient with a leg ulcer firstly by winding the leg with an even layer of the highly absorbent bandage and secondly by winding the leg with an elastic bandage applied over the highly absorbent bandage to generate sufficient sub-bandage pressure. This elastic bandage is preferably of the type disclosed in PCT/GB 93/02469 to Brightwake Ltd or that marketed under the name SETOPRESS™ by Seton Healthcare Group of Oldham, England or that marketed under the name of TENSOPRESS™ by Smith and Nephew Ltd. In a preferred embodiment the bandaging system comprises a dressing applied to and in contact with the wound such as an occlusive hydrocolloid dressing such as GRANUFLEX™ or a fibrous dressing such as KALTOSTAT™.

What is claimed is:

1. A method of treating a leg ulcer comprising:
   applying a highly absorbent bandage which comprises at least 5% by weight of a highly absorbent fibre and up to 10% by weight of a bicomponent fibre to cover (i) the ulcer or (ii) the ulcer covered by an occlusive hydrocolloid dressing; and applying as a second layer, an elastic bandage adapted to apply pressure to the highly absorbent bandage covering the ulcer.

2. The method as claimed in claim 1, wherein said bandaging system is applied:
   (a) by winding the leg with an even layer of the highly absorbent bandage; and
   (b) by winding the leg with the elastic bandage over the highly absorbent bandage.

3. The method of claim 1, wherein the highly absorbent bandage is applied to cover the ulcer.

4. The method of claim 3, wherein the highly absorbent bandage is adapted to absorb and retain at least 25 g water per g highly absorbent bandage.

5. The method of claim 3, wherein the highly absorbent bandage comprises between 5% and 50% by weight of a highly absorbent fibre.

6. The method of claim 3, wherein the highly absorbent bandage comprises between 10% and 15% by weight of a highly absorbent fibre.

7. The method of claim 1, wherein the highly absorbent bandage is applied to cover the ulcer covered by an occlusive hydrocolloid dressing.

8. The method of claim 7, wherein the highly absorbent bandage is adapted to absorb and retain at least 25 g water per g bandage.

9. The method of claim 7, wherein the highly absorbent bandage comprises between 5% and 50% by weight of a highly absorbent fibre.

10. The method of claim 7, wherein the highly absorbent bandage comprises between 10% and 15% by weight of a highly absorbent fibre.

11. The method of claim 1, wherein the ulcer is located at or adjacent to the ankle and the second bandage is wrapped around the ankle with a pressure of 25 to 40 mm Hg.

12. The method of claim 1, wherein the ulcer is located at or adjacent to the calf and the second bandage is wrapped around the calf with a pressure of 15 to 20 mm Hg.

* * * * *